US007331936B2

(12) United States Patent
Liu (10) Patent No.: US 7,331,936 B2
(45) Date of Patent: Feb. 19, 2008

(54) CYLINDRICAL PUSHROD FOR NEEDLE-RETRACTING SAFETY INJECTOR AND THE NEEDLE-RETRACTION CONTROLLABLE SAFETY INJECTOR

(76) Inventor: Wenjie Liu, Beijing WanTeFu Medical Apparatus Co., Ltd., Niantou Park, Machikou Town, Changping District, Beijing (CN) 102200

( * ) Notice: Subject to any disclaimer, the term of this patent is extended or adjusted under 35 U.S.C. 154(b) by 265 days.

(21) Appl. No.: 11/227,104

(22) Filed: Sep. 16, 2005

(65) Prior Publication Data
US 2006/0253083 A1    Nov. 9, 2006

(30) Foreign Application Priority Data
Apr. 26, 2005    (CN)    .................. 2005 1 0066442

(51) Int. Cl.
*A61M 5/00*    (2006.01)
*A61M 5/32*    (2006.01)
*F02M 47/02*    (2006.01)

(52) U.S. Cl. ..................... 604/110; 604/181; 604/192; 604/194; 604/195; 604/198; 239/88; 239/89

(58) Field of Classification Search .................. 239/88, 239/89, 585.5, 589; 604/110, 198, 194, 181, 604/192, 195
See application file for complete search history.

(56) References Cited

U.S. PATENT DOCUMENTS 5,360,410 A * 11/1994 Wacks ........................ 604/232
5,460,611 A * 10/1995 Alexander .................. 604/110
5,720,727 A *  2/1998 Alexander et al. .......... 604/110
6,368,303 B1 *  4/2002 Caizza ........................ 604/110
6,632,198 B2 * 10/2003 Caizza ........................ 604/110

\* cited by examiner

*Primary Examiner*—Davis D. Hwu
(74) *Attorney, Agent, or Firm*—Pillsbury Winthrop Shaw Pittman, LLP (57) ABSTRACT

The invention provide a cylindrical pushrod for the syringe needle-retracting safety injector, comprising an outer cylinder, an inner cylinder, a push pole, an underpinned piece and a seal gasket; the push pole is set at the front end of chamber of outer cylinder, its front end appears as a tubular shape or projects partially in the longitudinal direction, the back end of push pole is supported on the underpinned piece; the underpinned piece is set at the front end of the chamber of outer cylinder and supports the push pole; the cylinder wall of the inner cylinder supports the underpinned piece; a clamping structure is set at the tail of this cylindrical pushrod. With the safety injector with the cylindrical pushrod according to the invention, the medical personnel can control the time of the needle retraction as desired, and is not necessary to change their habitual injection practice, and thereby the safety injector is easy to operate. The invention also provide a safety injector, which can not only carry out the controllable retraction of the needle but also has a simple and crafty fixed structure of the needle stand to achieve the effect of reliable fixation as well as releasing with ease.

20 Claims, 11 Drawing Sheets

CYLINDRICAL PUSHROD FOR NEEDLE-RETRACTING SAFETY INJECTOR AND THE NEEDLE-RETRACTION CONTROLLABLE SAFETY INJECTOR

CROSS REFERENCE TO RELATED APPLICATIONS

This application claims priority under the provisions of 35 U.S.C. §119 of Chinese Patent Application No. 200510066442.7 filed on Apr. 26, 2005, which is hereby incorporated by reference in its entirety.

FIELD OF THE TECHNOLOGY

This invention relates to a medical instrument, and particularly to a cylindrical pushrod for the needle-retracting safety injector, and the needle-retracting controllable safety injector having the said pushrod.

BACKGROUND OF THE INVENTION

The injector is a medical instrument used commonly and in large quantities in the medical field. If the injector is used repeatedly, it is apt to lead to the spread of diseases between various patients and result in the cross contamination, which endanger the public health. Some people collect the waste single-use injectors that have already been used, and sale them in the medical market again for the illegal benefits, which bring the enormous hidden dangers of propagation and spread of various diseases. Moreover, when the medical personnel injects, the exposed needle may stab the medical personnel or the collector of castoff thereby causing the infection and propagation of diseases. In order to prevent the injector from being reused and achieve the object of single use by destructing the injector automatically after being used once, and in order to prevent the occurrence of accidental stabbing by the used injector, the technical schemes of the single-use injector with retractable syringe needle are proposed, such as the Chinese utility model patent No. ZL01221139.7, which disclosed a safety self-destructing single-use injector with the needle retracting into the inside of the injector after injecting. This technical schemes includes fixing the needle in the needle stand with a casing spring, the needle stand then being fixed in the head portion of the injector with the needle gasket, and at the end of injection, the pushrod's bottom plug fixed on the head of pushrod releasing the fit between the needle stand and the gasket through pushing and pressing, while the pushrod's bottom plug being pressed into the inside of hollow pushrod, and the whole needle together with the needle stand being retracted backward to the inside of the pushrod under the action of the spring, thereby achieving the self-destruction of injector so as to its reuse is avoided and the occurrence of stabbing accident due to the exposure of the needle after injection is excluded.

Though this technical scheme can carry out the retraction of the injector's needle after injection, the retraction process is performed automatically and is uncontrollable. Therefore, the technical solution exists the disadvantages as follows: first, the retraction is performed when the needle still stays in the patient's body while the injection is finished, which may cause the needle to push forward or sway when releasing the fixed structure of needle stand, thereby paining the patients or even hurt them; second, according to the operation criterion, the medical personnel should press the injection location with the sterilized cotton ball at the end of injection and then draw out the needle. However, the retraction of needle is automatic in this technical scheme and can not be controlled by the medical personnel, so the medical personnel must press the injection location with the sterilized cotton ball before the end of injection, which brings the operational inconvenience for the medical personnel because they must change their customary injection practice.

And in the technical scheme, the fixed structure of needle stand also exists defects that it can not obtain the fixed effect of being firm as well as releasable. Furthermore, the technical scheme also exists the defects that the needle stand is pushed forward to further penetrate into the patient's body when the bottom plug of the pushrod pushes and presses the fixed structure of needle stand and that the residual liquor is too much.

SUMMARY OF THE INVENTION

One purpose of the invention is to overcome the above-said defects of prior art, and provides a cylindrical pushrod that is used for the syringe needle-retracting safety injector and can carry out the controllable retraction of needle, and a needle-retraction-controllable safety injector with the cylindrical pushrod.

Another purpose of the invention is to provide a needle-retraction-controllable safety injector wherein the needle stand is fixed firmly at the head portion of injector with a simple fixed structure and is easy to be released, and which can realize that the needle stand and the needle will not moves further forward or sways unintentionality, and the residual drug liquor can be reduced effectively after injection.

In order to attain the said purposes of the invention, there provides a cylindrical pushrod for the syringe needle-retracting safety injector, wherein the cylindrical pushrod comprises an outer cylinder 1, an inner cylinder 2, a push pole 3 and an underpinned piece 4; the head of outer cylinder 1 is provided with a sealing gasket 5; the push pole 3 is set at the front end of chamber of outer cylinder 1, the front end of push pole 3 closes the frontend opening of outer cylinder 1 and outstands outside of the seal gasket 5, and appears as a tubular shape or projects partially in longitudinal direction, and the back end of said push pole 3 is supported on the underpinned piece 4; the underpinned piece 4 has a through hole 401 for allowing the push pole 3 to pass through and a underpinned patch 402 for opening or closing the through hole 401, and the underpinned patch 402 is set at the front end of the chamber of outer cylinder 1 and supports the push pole 3; the inner cylinder 2 is set inside the outer cylinder 1 with its front end openend and its back end closed, and the top end surface of its cylinder wall supports the underpinned piece 4 or the underpinned patch 402 thereof to close the through hole 401; the tail of cylindrical pushrod is provided with a clamping structure for clamping the inner cylinder and the outer cylinder in a releasable manner, the clamping structure may make the inner cylinder 2 slide backward for a distance for allowing the push pole 3 pass through after opening the through hole 401 under the action of retractive force of the needle, and is clamped within the outer cylinder 1 again after it is released to.

As a modified cylindrical pushrod for the needle-retracting safety injector of the invention, wherein the clamping structure is a supporting piece 6, which is composed of one O-shape ring part 601, two elastic strips 602 and two raised blocks 603; the two elastic strips 602 are set opposing to each other at both sides of the O-shape ring part 601; the two raised blocks 603 are set respectively at the position on the outside of two elastic strips 602 with the same height, and the two raised blocks 603 are of the semispherical, triangle shape or the other shapes with a slope on its upside; the cylinder wall of outer cylinder 1 is provided respectively with the holes 101 having a matched shape with the raised blocks 603 in the position matching with the two raised blocks 603; after the supporting piece 6 is mounted, the two raised blocks 603 engage into the holes 101 respectively and protrude beyond the holes 101; the cylinder wall of rear portion of inner cylinder 2 exists two long holes 201 opposing to each other; the supporting piece 6 is set around the rear portion of inner cylinder 2 in the position of the long hole 201 and engaged in the holes 101 of outer cylinder 1, and the upper end of elastic strips 602 supports the superior border's surface of the long hole 201 of inner cylinder 2.

As a modified cylindrical pushrod for the needle-retracting safety injector according to the invention, wherein the cylinder wall of rear portion of the outer cylinder 1 has at least one long hole 102; the cylinder wall of mid-back portion of inner cylinder 2 has the corresponding long holes 202 at the position matched with the long hole 102, the superior border of the long holes 202 extends downward to form an upright or inclining outward elastic strips 203, and there are two raised blocks, the upper raised block and the lower raised block, on the outside wall of the elastic strips 203, the distance between the lower end surface of upper raised block 204 and the lower end surface of lower raised block 205 equals to or exceeds the distance of inner cylinder 2 sliding backward for opening the through hole 401 to allow the push pole 3 passes through, the height of the upper raised block 204 equals to or exceeds that of the lower raised block 205, and a slope is formed on the top thereof, the upper and lower raised blocks are fixed in and protrude outside the long holes 102, and the lower raised block 205 is supported on the inferior border of the long hole 102 so that the inner cylinder 2 can be locked releasably on the outer cylinder 1.

As a modified cylindrical pushrod for the needle-retracting safety injector according to the invention, wherein the chamber of outer cylinder 1 contracts inward to form a shoulder 103 at the front end of outer cylinder 1, and extends forward to form a hollow chamber with a smaller diameter; the underpinned piece 4 is a O-shape sheet with a through hole 401 at its center, and is provided with a plurality of upwarping elastic underpinned patchs 402; the underpinned piece 4 is set at the front end of the chamber of outer cylinder 1, and the top end surface of inner cylinder 2 pushes and presses the underpinned piece 4 to the shoulder 103 of the front end of chamber of outer cylinder 1 to press down the elastic underpinned patchs 402 which then occlude the through hole 401 and support the push pole 3; the push pole 3 is set in the hollow chamber with the smaller diameter at the front end of outer cylinder 1.

As a cylindrical pushrod for the needle-retracting safety injector according to the invention, wherein the underpinned piece 4 is compose of a plug 7 and an underpinned patch 8, the connection between the underpinned patch 8 and the plug 7 is a flexible connection, and a hinge structure, a gemel structure or the like can be set between the underpinned patch 8 and the plug 7, or the joint part can be formed as a flexional feeble layer, to realize the flexible connection between the two parts; an aperture through which the underpinned patch 8 passes and which has a shape matching with the plug is provided on the cylinder wall of the front end of outer cylinder 1; after the underpinned patch 8 is inserted into the aperture, the plug 7 closes the aperture and secures one end of the underpinned patch 8 on the cylinder wall of outer cylinder 1, the other end of the underpin patch 8 is supported on the top end surface of the cylinder wall of inner cylinder 2.

As a modified cylindrical pushrod for the needle-retracting safety injector according to the invention, wherein the underpinned piece 4 is a ring part, on which a through hole 401 and an underpinned patch 402 are provided, and a round of groove or flange 403 playing the function of clamping is provided on its side wall, one end of the underpinned patch 402 is free, and the other end of the underpinned patch connects to the underpinned piece 4 with a hinge, a gemel or the like, or a flexional feeble layer to achieve a flexible connection; the underpinned piece 4 is set at the front end of the chamber of outer cylinder 1, a round of flange or groove 105 are provided on the cylinder wall of the front end of outer cylinder 1 to match with the groove or flange 403 on the underpinned piece 4, and the underpinned piece 4 is fixed at the front end of chamber of outer cylinder 1 through the clamping function of the groove and flange; the top end surface of the cylinder wall of inner cylinder 2 supports the free end of the underpinned patch 402 to close the through hole 401.

As a modified cylindrical pushrod for the needle-retracting safety injector according to the invention, it further comprises a protective sleeve 9 which function to protect the clamping structure set at the tail of the cylindrical pushrod from being disengaged unintentionally due to accidental touch, the protective sleeve 9 is a jointed body of a thick cylinder 901 and a thin cylinder 902; a round of flange 106 is set on the outer wall of the rear portion of outer cylinder 1; the inner diameter of thin cylinder 902 matches with the outer diameter of outer cylinder 1, a round of groove 903 is set on the inside wall of the thin cylinder 902 to clamp with the flange 106, the protective sleeve 9 is connected to the rear end of outer cylinder 1 and is fixed by the clamping relation between the groove 903 and the flange 106, the thick cylinder 901 of the protective sleeve 9 covers the clamping structure after being mounted.

As a modified cylindrical pushrod for the needle-retracting safety injector according to the invention, wherein it further comprises a sealing gasket 10; the chamber of outer cylinder 1 contracts inward to form a shoulder 103 at the front end of outer cylinder 1; an annular dummy club 301 is set at the lower end of push pole 3; the sealing gasket 10 is mounted between the annular dummy club 301 and the shoulder 103 at the front end of the chamber of outer cylinder 1.

As a modified cylindrical pushrod for the needle-retracting safety injector according to the invention, wherein it further comprises a compressible needle-stopping piece 11; a hollow chamber is set at the front end of push pole 3; the needle-stopping piece 11 is set within the hollow chamber at the front end of push pole 3, the needle-stopping piece 11 has an exposed part at the front end which is higher than the front end of push pole 3 after plugging the opening of the hollow chamber of push pole 3, and the compressive force of the needle-stopping piece 11 is larger than or equal to the retractive force of the needle.

As a modified cylindrical pushrod for the needle-retracting safety injector according to the invention, wherein the needle-stopping piece 11 is composed of a piston head 1101 and a compressible part, the compressible part may be a hollow thinwall pipe 1102 or a hollow corrugated pipe, and also may be a spring supporting the piston head.

As a modified cylindrical pushrod for the needle-retracting safety injector according to the invention, wherein a groove 1105 is set on the top surface of the needle-stopping piece 11; a slot 302 communicated with the groove 1105 is set in the chamber wall of the hollow chamber at the front end of push pole 3. The purpose of the groove 1105 and the slot 302 is to push out the drug liquor in the syringe as much as possible to reduce the remains of drug liquor.

As a modified cylindrical pushrod for the needle-retracting safety injector according to the invention, wherein the outer cylinder 1 shows up a front end in a tubular shape or with partial longitudinal projection after the seal gasket 5 is installed thereon; the push pole 3 is changed into a compressible needle-stopping piece 12, the front end of the needle-stopping piece 12 plugs into the opening of the hollow chamber of outer cylinder 1 and has an exposed part at its front end which is higher than the front end of outer cylinder 1, the rear end of the needle-stopping 12 is compressible and is supported on the underpinned piece 4, the compressive force of the needle-stopping piece 12 exceeds or equals to the retractive force of the needle.

As a modified cylindrical pushrod for the needle-retracting safety injector according to the invention, wherein the needle-stopping piece 12 is composed of a piston head 1201 and a compressible part; the piston head 1201 plugs into the opening of the hollow chamber of outer cylinder 1 and has an exposed part which is higher than the front end of outer cylinder 1; the compressible part may be a hollow thinwall pipe 1202 or a hollow corrugated pipe 1203, and also may be a spring supporting the piston head.

As a modified cylindrical pushrod for the needle-retracting safety injector according to the invention, wherein the rear end of the needle-stopping piece 12 is provided with a supporting dummy club 1205 which matches with the shoulder positioned at the top end of chamber of the outer cylinder 1.

As a modified cylindrical pushrod for the needle-retracting safety injector according to the invention, wherein on the top surface of needle-stopping piece 12 is provided with a groove 1206; a slot communicated with the groove is provided on the cylinder wall at the position of the frontend opening of outer cylinder 1.

In order to attain the said purposes of the invention, there also provides a needle-retraction controllable safety injector, wherein the said safety injector is mounted with a cylindrical pushrod for the needle-retracting safety injector structured as above.

As a modified needle-retraction controllable safety injector according to the invention, wherein the safety injector comprises a needle syringe 13, a needle stand 14 for fixing a needle, a needle stand sheath 15, a spring 16, a needle stand fixture and a cylindrical pushrod with the abovesaid structure; the needle syringe 13 forms a shoulder of contracting inward at its distal end, and the shoulder extends outward to form a cannula 17 with a less diameter than that of the needle syringe 13, the inside wall is provided with a round of flange 18 at the connection position of the shoulder with the cannula 17, and the outer wall of cannula 17 is provided with a round of flange or groove 1701; the needle stand 14 is a tubular body with a through hole 1401 in its center, the needle is fixed in the through hole 1401 of the needle stand 14, the lower end of needle stand 14 is provided with a dummy club 1402, and the needle stand 14 is installed within the cannula 17; the said needle stand fixture comprises the flange 18, the dummy club 1402 and an O-shape seal ring 19, the said O-shape seal ring 19 is set around the lower portion of dummy club 1402 of the needle stand 14, the flange 18 supports the O-shape seal ring 19, and the O-shape seal ring 19 supports the dummy club 1402 of the needle stand 14, thereby the needle stand 14 is removably fixed in the cannula 17; the spring 16 is set around the needle stand 14 with its lower end supported on the dummy club 1402 of the needle stand 14; the needle stand sheath 15 has a hollow chamber opening rearward, the inner diameter of the chamber matches with the outer diameter of cannula 17, and the inside wall is provided with a round of groove or flange 1501 clamping with the flange or groove 1701 on the outer wall of cannula 17, the closed top end of needle stand sheath 15 has a through hole 1502, the needle stand sheath 15 is installed on the cannula 17 mounted already with the needle stand 14, the needle 1 extendes out from the through hole 1502, the closed top end of needle stand sheath 15 press the upper end of spring 16 and prepress the spring 16 between the closed top end and the dummy club 1402 of the needle stand 14, and then the lower border surface of the closed top end joints with the upper border surface of the top end of needle stand 14; the said cylindrical pushrod is installed within the needle syringe 13, the thick cylinder 901 of its protective sleeve 9 is connected around partly on the outer wall of the rear end of needle syringe 13, when the cylindrical pushrod is pushed to the top end of the chamber of needle syringe 13, i.e. when the injection is complete, the top end of cylindrical pushrod drives the O-shape seal ring 19 to slide as a whole or partially so as to loose the needle stand fixture and release the needle stand 14, at the same time, the lower border surface of needle syringe 13 push to disengage the clamping structure of the rear end of the cylindrical pushrod and releases the inner cylinder 2.

As a modified needle-retraction controllable safety injector according to the invention, which comprises a needle syringe 13, a needle stand 14 for fixing a needle, a needle stand sheath 15, a spring 16, a needle stand fixture and a cylindrical pushrod with the abovesaid structure but without the protective sleeve 9; the needle syringe 13 forms a shoulder of contracting inward at its distal end, and the shoulder extends outward to form a cannula 17 with a less diameter than that of the needle syringe 13, the inside wall is provided with a round of flange 18 at the connection position of the shoulder with the cannula 17, and the outer wall of cannula 17 is provided with a round of flange or groove 1701; the needle stand 14 is a tubular body with a through hole 1401 in its center, the needle is fixed in the through hole 1401 of the needle stand 14, the lower end of needle stand 14 is provided with a dummy club 1402, and the needle stand 14 is installed within the cannula 17; the said needle stand fixture comprises the flange 18, the dummy club 1402 and an O-shape seal ring 19, the said O-shape seal ring 19 is set around the lower portion of dummy club 1402 of the needle stand 14, the flange 18 supports the O-shape seal ring 19, and the O-shape seal ring 19 supports the dummy club 1402 of the needle stand 14, thereby the needle stand 14 is removably fixed in the cannula 17; the spring 16 is set around the needle stand 14 with its lower end supported on the dummy club 1402 of the needle stand 14; the needle stand sheath 15 has a hollow chamber opening rearward, the inner diameter of the chamber matches with the outer diameter of cannula 17, and the inside wall is provided with a round of groove or flange 1501 clamping with the flange or groove 1701 on the outer wall of cannula 17, the closed top end of needle stand sheath 15 has a through hole 1502, the needle stand sheath 15 is installed on the cannula 17 mounted already with the needle stand 14, the needle 1 extendes out from the through hole 1502, the closed top end of needle stand sheath 15 press the upper end of spring 16 and prepress the spring 16 between the closed top end and the dummy club 1402 of the needle stand 14, and then the lower border surface of the closed top end joints with the upper border surface of the top end of needle stand 14; the said cylindrical pushrod is installed within the needle syringe 13, when the cylindrical pushrod is pushed to the top end of the chamber of needle syringe 13, the top end of cylindrical pushrod drives the O-shape seal ring 19 to slide as a whole or partially so as to loose the needle stand fixture and release the needle stand 14, at the same time, the lower border surface of needle syringe 13 push to disengage the clamping structure of the rear end of the cylindrical pushrod and releases the inner cylinder 2.

As a modified needle-retraction controllable safety injector according to the invention, wherein a protective patch 21 is provided between the roll rim 20 of the needle syringe 13 and the protective sleeve 9 to prevent the cylindrical pushrod from being pushed to the top end of the chamber of needle syringe 13 and the needle stand 14 and the clamping structure being loosed prior to the use of the injector due to a misoperation; the protective patch 21 can be fixed on the lower end surface of the roll rim 20, and also can be fixed on the cylinder wall of the needle syringe 13 or the protective sleeve 9.

By comparison with the prior art, the cylindrical pushrod and the safety injector provided by the invention can achieve the following advantageous technical effects:

First, in the safety injector mounted with the cylindrical pushrod according to the invention, even the needle stand 14 and the inner cylinder 2 are all in a releasing state after the injection is complete, the released needle stand still maintain its original position without retractation, because the operator still presses the rear end of the cylindrical pushrod with his/her finger, which makes the released inner cylinder 2 can not slide backward and the through hole 401 on the underpinned piece 4 can not be opened. As such, the operator can loose the finger pressing on the rear end of cylindrical pushrod after he(she) draws out the needle soas to let the needle retract into the injector. Therefore, the operator can control the time of the needle's retraction at his own will, and need not to change his operation practice. It facilitate the operation.

Second, the safety injector according to the invention not only can carry out the controllable needle-retraction but also has a simple and crafty fixed structure of the needle stand, to achieve the effect of reliability as well as releasing with ease, and the needle stand can not move forward or sway unintentionally during being released to injure the patient.

Third, the safety injector with the cylindrical pushrod according to the invention can push out the drug liquor in the needle syringe as much as possible before the needle-retraction to reduce the remains of drug liquor.

DETAILED DESCRIPTION OF THE INVENTION

The embodiments of the invention will be explained detailedly with reference to the accompanying drawings hereinafter.

Figure 1:
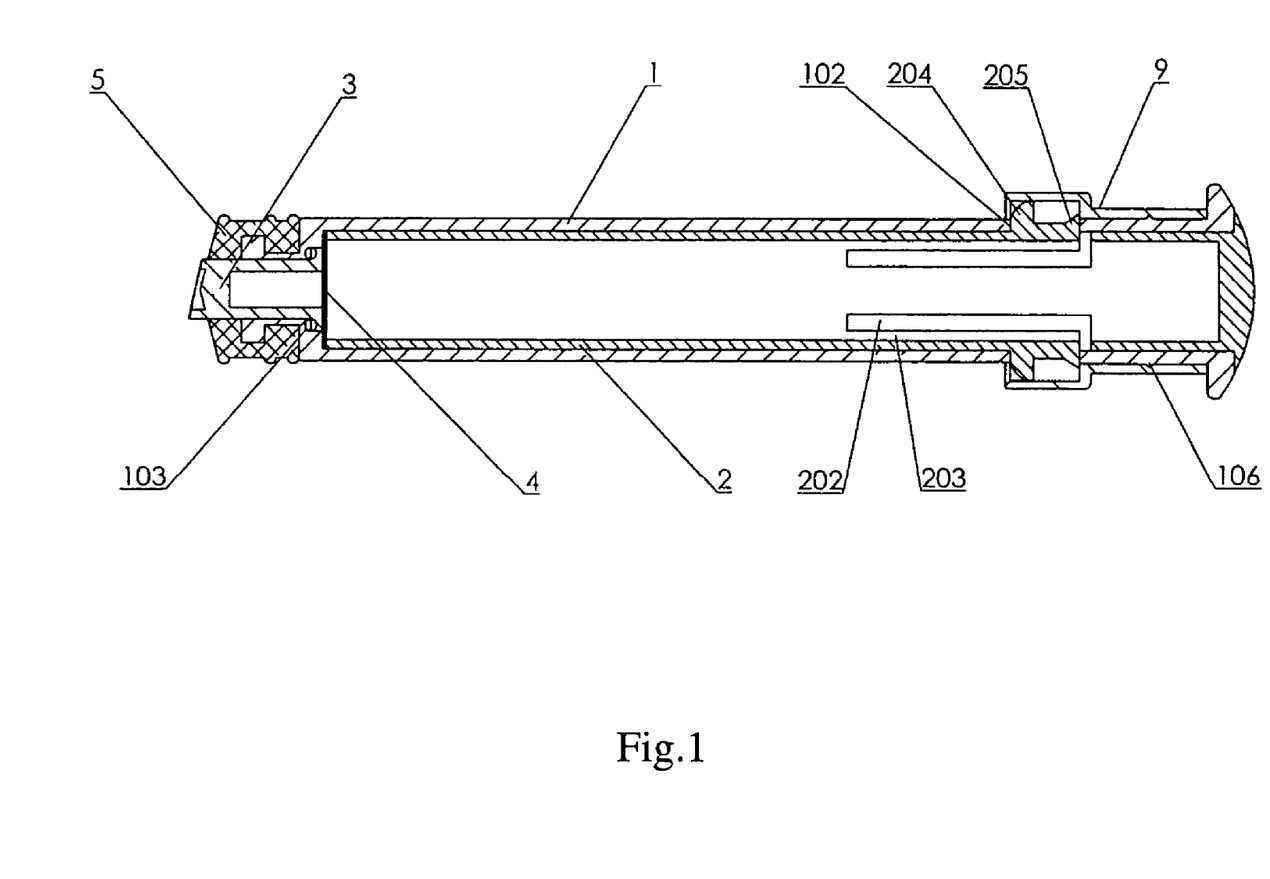
FIG. 1 is a section view of a cylindrical pushrod as one of the embodiments of the invention.
Figure 2:
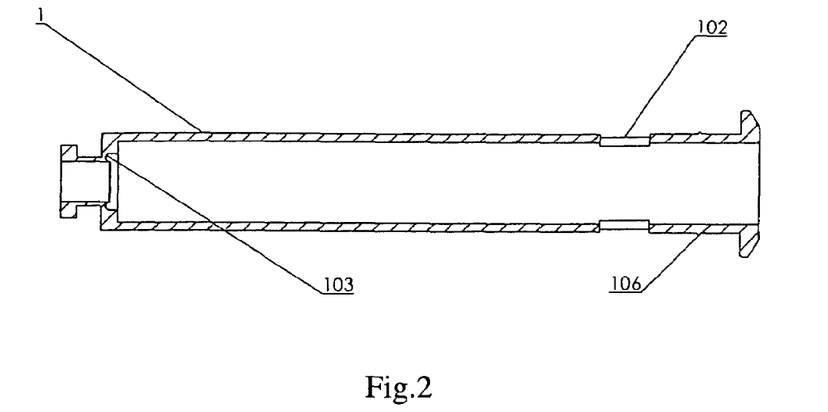
FIG. 2 is a section view of the outer cylinder of the cylindrical pushrod as shown in FIG. 1.
Figure 3:
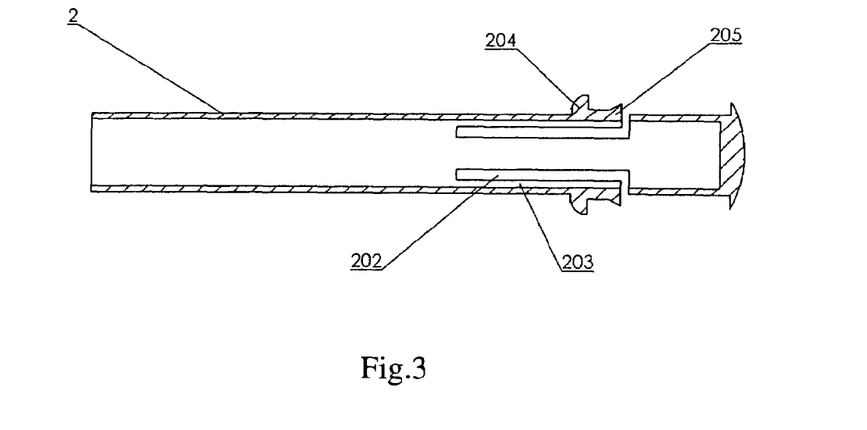
FIG. 3 is a section view of the inner cylinder of the cylindrical pushrod as shown in FIG. 1.
Figure 4:
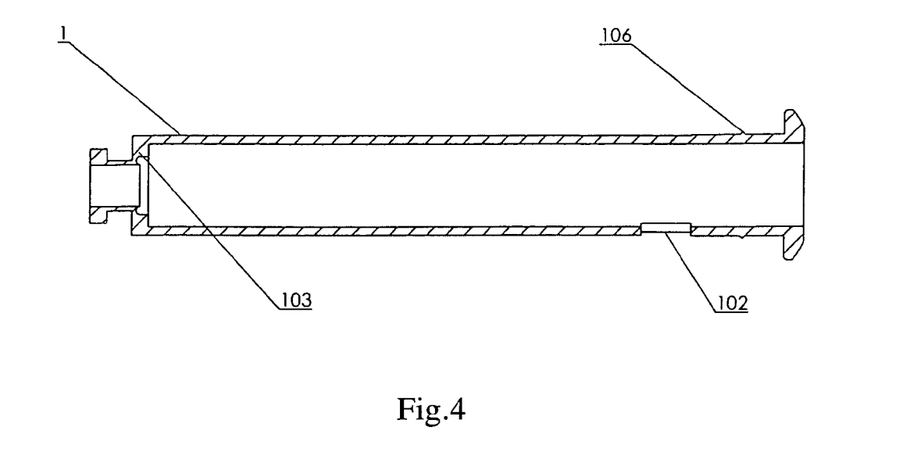
FIG. 4 is a section view of the outer cylinder used in another embodiment of the invention.
Figure 5:
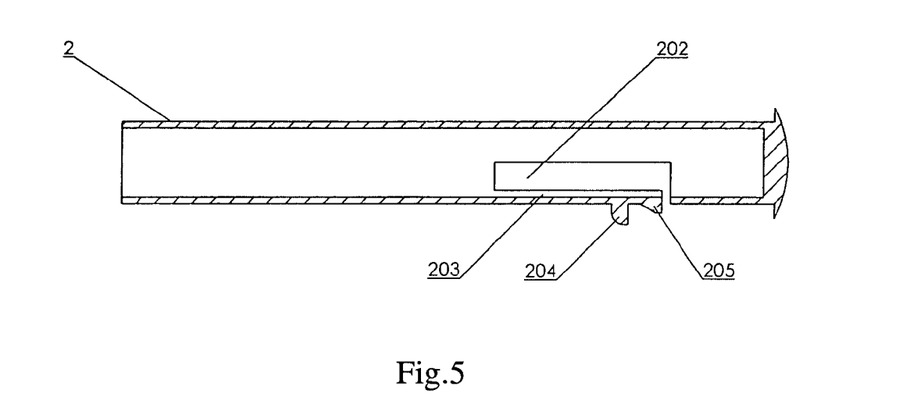
FIG. 5 is a section view of the inner cylinder matching with the outer cylinder as shown in FIG. 4.
Figure 6:
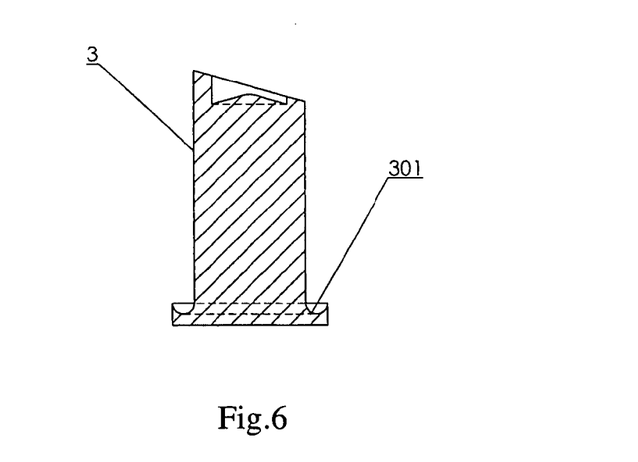
FIG. 6 is a section view of a push pole according to the invention.
Figure 7:
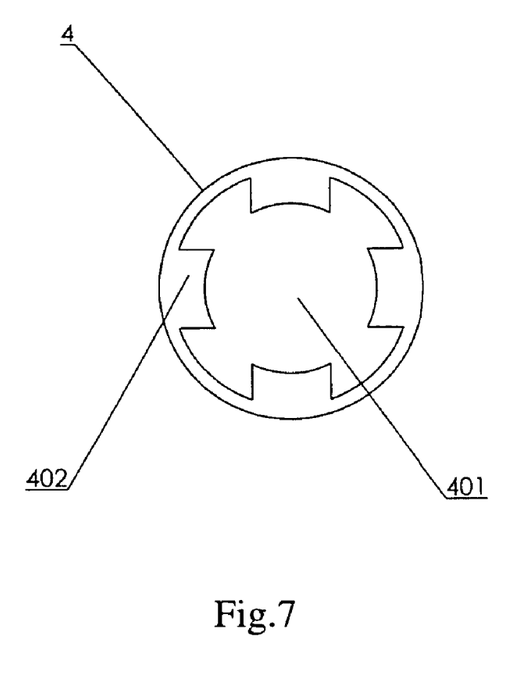
FIG. 7 is a top view of an underpinned piece according to the invention.
Figure 8:
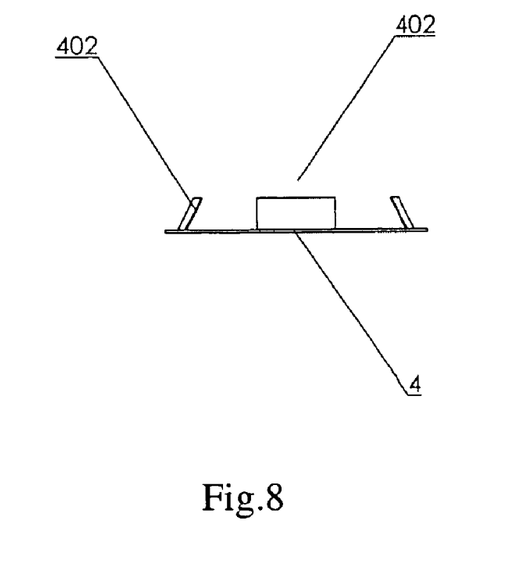
FIG. 8 is a side view of the underpinned piece shown in FIG. 7.
Figure 13:
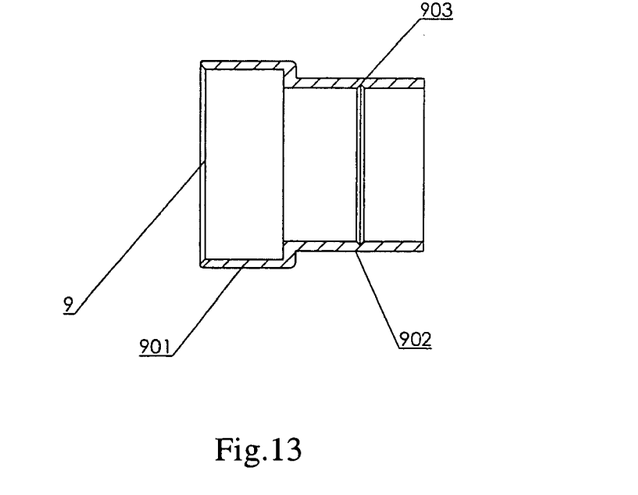
FIG. 13 is a section view of the protective sleeve in the cylindrical pushrod shown in FIG. 1.

The first embodiment: as shown in FIGS. 1-8 and 13, the cylindrical pushrod for the needle-retracting safety injector according to this embodiment, comprises an outer cylinder 1, an inner cylinder 2, a push pole 3, an underpinned piece 4 and a protective sleeve 9;

Around the head of outer cylinder 1 is provided with a sealing gasket 5;

The chamber of outer cylinder 1 contracts inward to form a shoulder 103 at the front end of outer cylinder 1, and extends forward to form a hollow chamber with a smaller diameter;

The push pole 3 is set in the hollow chamber with the smaller diameter at the front end of outer cylinder 1, with its outer wall jointing with the inside wall of the front end of outer cylinder 1, the front end of push pole 3 closes the frontend opening of outer cylinder 1 and outstands outside of the seal gasket 5, and appears as a tubular shape or projects partially in longitudinal direction, and the back end of push pole 3 is supported on the underpinned piece 4;

The underpinned piece 4 is a O-shape sheet with a through hole 401 at its center, and is provided with four upwarping elastic underpinned patchs 402;

The underpin piece 4 is set at the front end of the chamber of outer cylinder 1, and the top end surface of inner cylinder 2 pushes and presses the underpinned piece 4 to the shoulder 103 of the front end of chamber of outer cylinder 1 to press down the elastic underpinned patchs 402 which then occlude the through hole 401 and support the push pole 3;

The inner cylinder 2 is set inside the outer cylinder 1 with its front end openend and its back end closed, and the top end surface of its cylinder wall supports the underpinned piece 4 to close the through hole 401;

An annular dummy club 301 is set at the lower end of push pole 3; a sealing gasket 10 is mounted between the annular dummy club 301 and the frontend wall of the chamber of outer cylinder 1;

The protective sleeve 9 is a jointed body of a thick cylinder 901 and a thin cylinder 902;

A round of flange 106 is set on the outer wall of the rear portion of outer cylinder 1; the inner diameter of thin cylinder 902 matches with the outer diameter of outer cylinder 1, a round of groove 903 set on the inside wall of the thin cylinder 902 to clamp with the flange 106, the protective sleeve 9 is connected around the rear end of outer cylinder 1 and is fixed by the clamping relation between the groove 903 and the flange 106, the thick cylinder 901 of the protective sleeve 9 covers the clamping structure after being mounted;

The clamping structure of the rear portion of cylindrical pushrod has the following structure:

The cylinder wall of rear portion of the outer cylinder 1 has two long hole 102;

The cylinder wall of mid-back portion of inner cylinder 2 has two corresponding long holes 202 at the position matched with the long hole 102, the upper border of long hole 202 extends downward to form an upright elastic strip 203, and there are two raised blocks, the upper raised block and the lower raised block, on the outside wall of the elastic strip 203, the distance between the lower end surface of upper raised block 204 and the lower end surface of lower raised block 205 equals the distance of inner cylinder 2 sliding backward for opening the through hole 401 to allow the push pole 3 passes through, the height of the upper raised block 204 exceeds that of the lower raised block 205, and a slope is formed on the top portions, the upper and lower raised blocks are fixed in and protrude outside the long holes 102, and the lower raised block 205 is supported on the lower border of the long hole 102 so that the inner cylinder 2 can be locked releasably on the outer cylinder 1;

After the inner cylinder disengages with the outer cylinder, the inner cylinder 2 slides backward under the action of retractive force of the pinhead to a distance so that the through hole 401 is opened to allow the push pole 3 passes through, and then the inner cylinder 2 is locked on the outer cylinder 1 again with the upper raised block 204.

Figure 15:
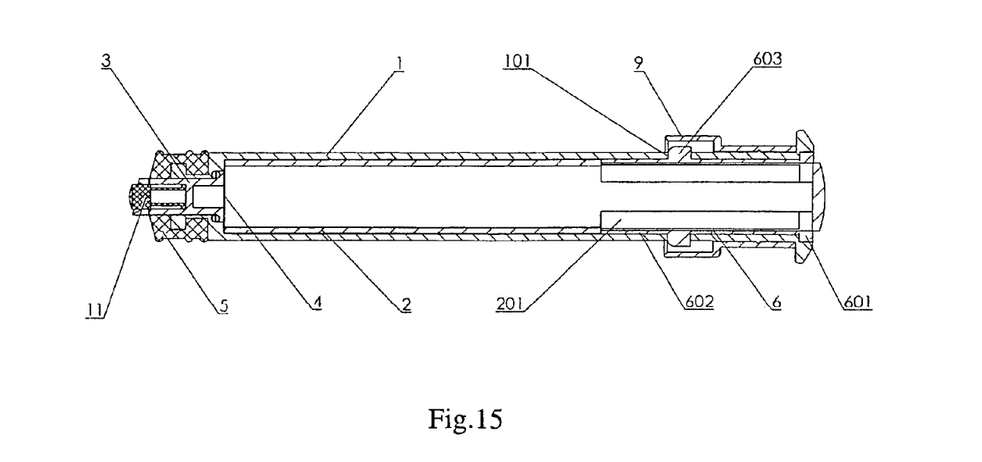
FIG. 15 is a section view of a cylindrical pushrod according to another embodiment of the invention.
Figure 16:
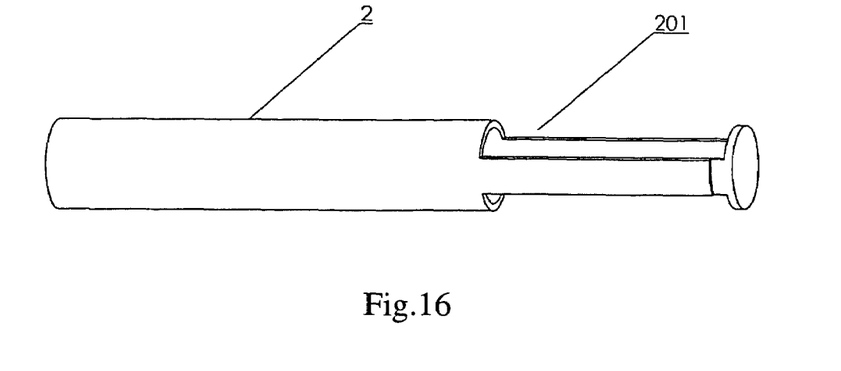
FIG. 16 is a schematic drawing of the inner cylinder of cylindrical pushrod shown in FIG. 15.
Figure 17:
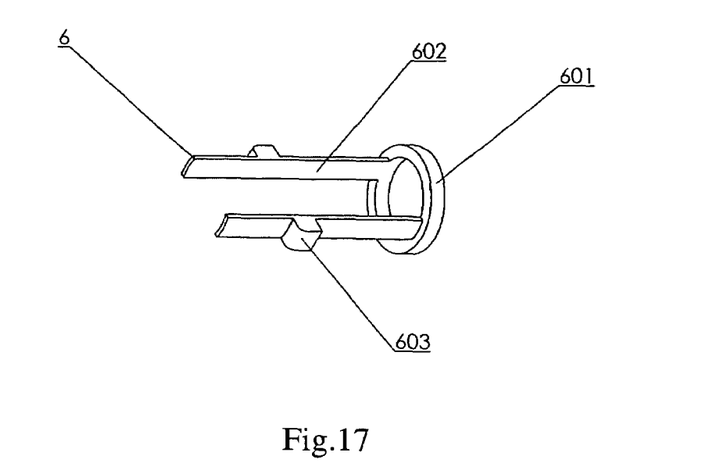
FIG. 17 is a schematic drawing of the supporting piece of cylindrical pushrod shown in FIG. 15.

The second embodiment: as shown in FIGS. 15-19, the basic structure of this embodiment is similar to that of the first embodiment, the differences include:

The clamping structure of the rear portion of the cylindrical pushrod comprises a supporting piece 6:

The supporting piece 6 is composed of one O-shape ring part 601, two elastic strips 602 and two raised blocks 603;

The two elastic strips 602 are set opposing to each other at both sides of O-shape ring part 601;

The two raised blocks 603 are set respectively at the position on the outside of two elastic strip 602 with the same height, and the two raised blocks 603 each has a slope on the top;

The cylinder wall of outer cylinder 1 is provided respectively with the holes 101 having a matched shape with the raised blocks 603 respectively in the position matching with the two raised blocks 603;

After the supporting piece 6 is mounted, the two raised blocks 603 engage into the holes 101 respectively and protrude beyond the holes 101;

The cylinder wall of rear portion of inner cylinder 2 exists two long holes 201 opposing to each other;

The supporting piece 6 is set around the rear portion of inner cylinder 2 in the position of the long holes 201 of and engaged in the holes 101 of outer cylinder 1, and the upper end of elastic strip 602 supports the superior border's surface of the long holes 201 of inner cylinder 2.

Figure 18:
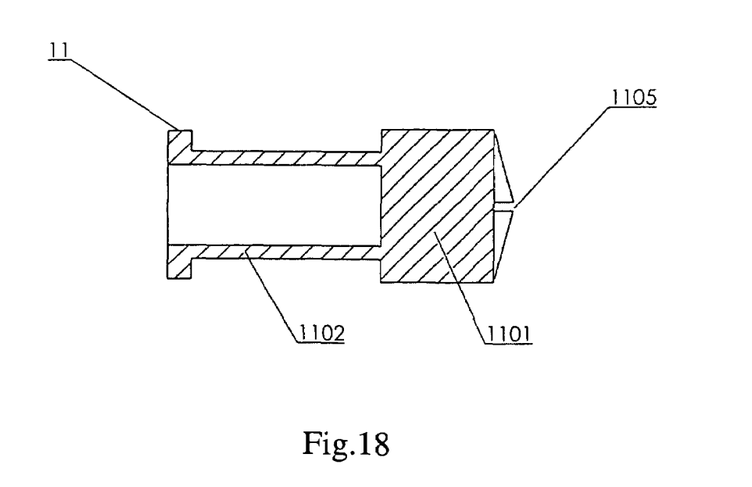
FIG. 18 is a section view of a needle-stopping piece according to the invention.
Figure 19:
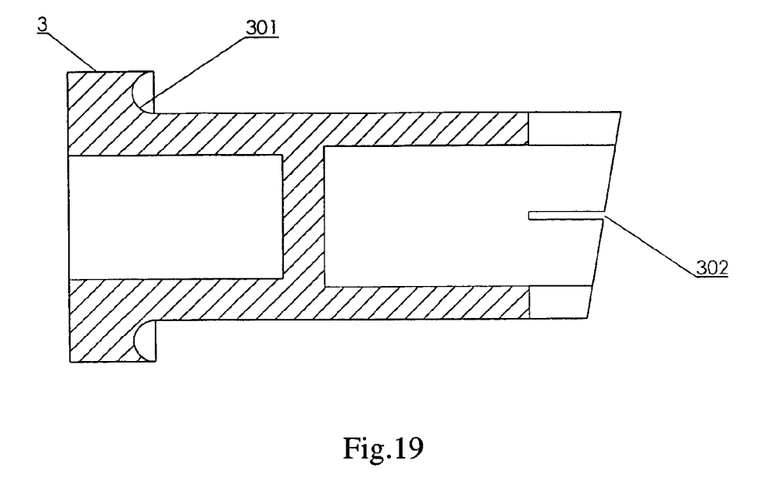
FIG. 19 is a section view of a push pole according to the invention.

The cylindrical pushrod in this embodiment further comprises a compressible needle-stopping piece 11;

The needle-stopping piece 11 is composed of a piston head 1101 and a compressible part, the compressible part is a hollow thinwall pipe 1102;

At the front end of push pole 3 is provided with a hollow chamber; the needle-stopping piece 11 is set within the hollow chamber at the front end of push pole 3, the needle-stopping piece 11 has an exposed part at the front end which is higher than the front end of push pole 3 after plugging the opening of the hollow chamber of push pole 3, and the compressive force of the needle-stopping piece 11 is larger than the retractive force of the needle;

A groove 1105 is set on the top surface of the needle-stopping piece 11;

A slot 302 communicated with the groove 1105 is set in the the chamber wall of the hollow chamber at the front end of push pole 3.

Figure 9:
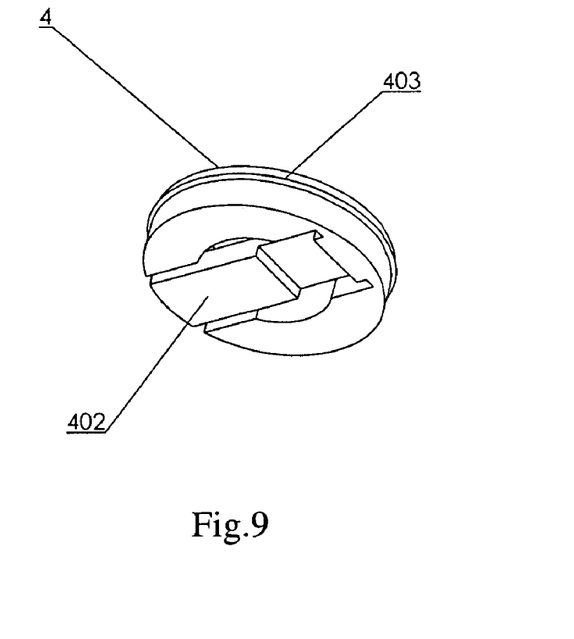
FIG. 9 is a schematic drawing of another underpinned piece according to the invention.
Figure 10:
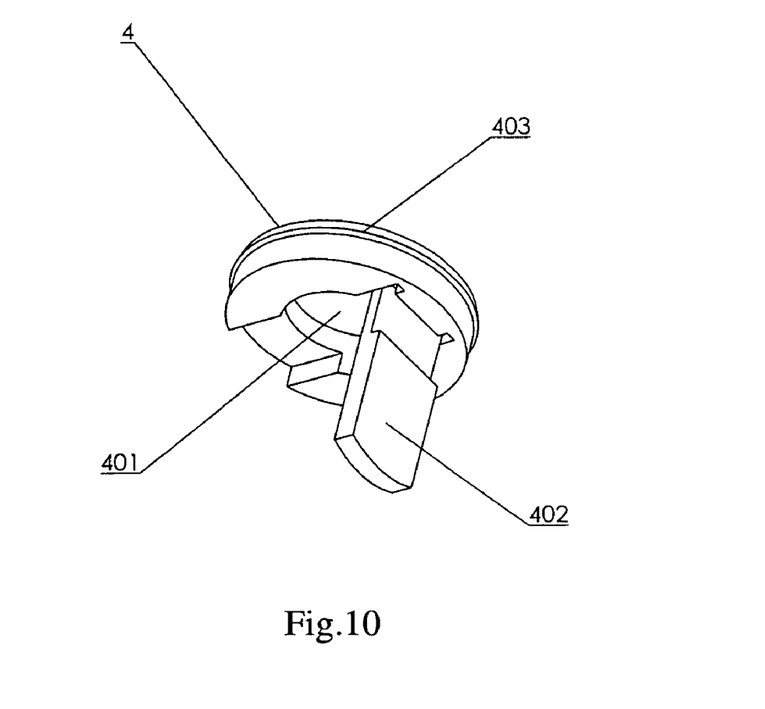
FIG. 10 is schematic drawing of the underpinned piece shown in FIG. 9 when the underpinned patch is unfolded.
Figure 11:
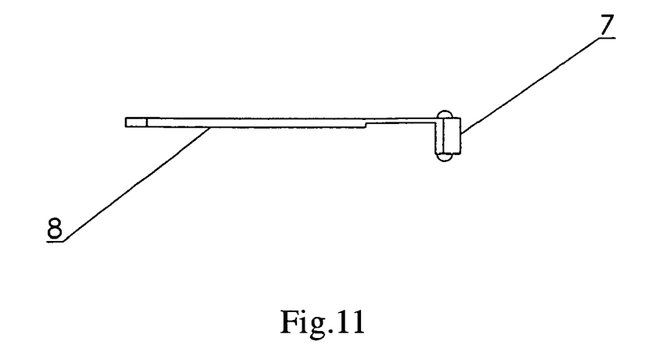
FIG. 11 is a schematic drawing of the other underpin piece put forward by the invention.
Figure 12:
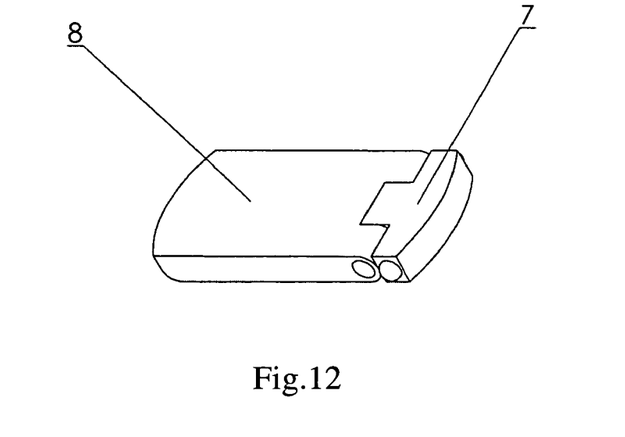
FIG. 12 is a schematic drawing of another underpinned piece according to the invention.
Figure 14:
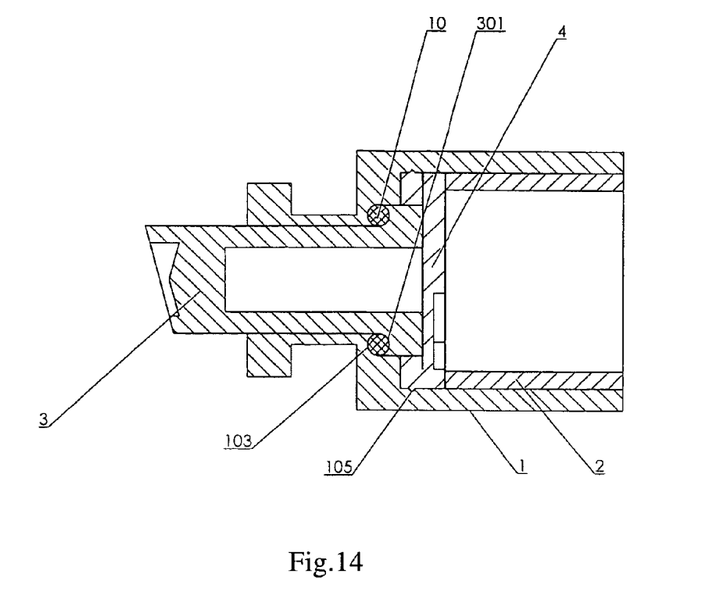
FIG. 14 is a partial section view of the cylindrical pushrod with the underpinned piece shown in FIG. 9.
Figure 20:
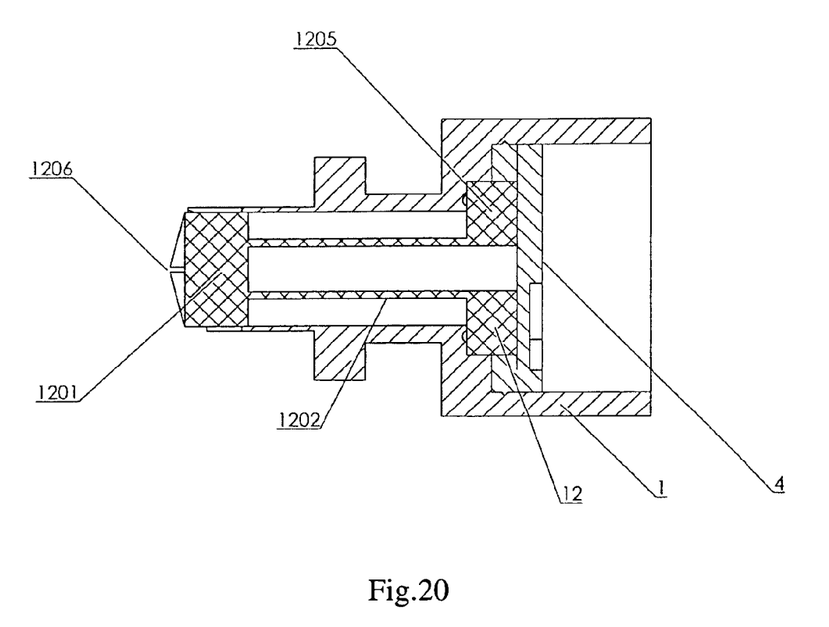
FIG. 20 is a partial section view of another cylindrical pushrod according to the invention.

The third embodiment: as shown in FIGS. 9, 10, 14, 20 and 21, the basic structure of this embodiment is similar to that of the first embodiment, the differences include:

The underpinned piece 4 is a ring part on which a through hole 401 and the underpinned patch 402 are provided, and a round of flange 403 playing the function of clamping is provided on its side wall, one end of the underpinned patch 402 is free, and the other end of the underpinned patch connects to the underpinned piece 4 with a flexional feeble layer;

The underpinned piece 4 is set at the front end of the chamber of outer cylinder 1, a round of groove 105 are provided on the cylinder wall of the front end in the chamber of outer cylinder 1 to match with flange 403 on the underpinned piece 4, and the underpinned piece 4 is fixed at the front end of the chamber of outer cylinder 1 through the clamping effect of the groove and flange;

The top end surface of the cylinder wall of inner cylinder 2 supports the free end of the underpinned patch 402 to close the through hole 401;

The push pole 3 can be changed into a compressible needle-stopping piece 12;

The needle-stopping piece 12 comprises a piston head 1201 and a compressible part, and its rear end is provided with a supporting dummy club 1205 matching with the shoulder at the top end of chamber of outer cylinder 1;

The front end of the piston head 1201 plugs into the opening of the hollow chamber of outer cylinder 1 and has an exposed part which is higher than the front end of outer cylinder 1;

The compressible part is a hollow thinwall pipe 1202, also may be a hollow corrugated pipe 1203, or may be a spring supporting the piston head 1201 (not shown in drawings);

The outer cylinder 1 shows up a front end in a tubular shape or with partial longitudinal projection after the seal gasket 5 is mounted thereon;

The front end of the needle-stopping piece 12 plugs into the opening of the hollow chamber of outer cylinder 1 and has an exposed part at its front end which is higher than the front end of outer cylinder 1, the rear end of this needle-stopping piece is compressible and is supported on the underpinned piece 4, the compressive force of the needle-stopping piece 12 is higher than the retractive force of the needle;

On the top end surface of the needle-stopping piece 12 is provided with a groove 1206;

On the cylinder wall of front end of outer cylinder 1 is provided with a slot for communicating with the groove (not shown in drawings).

Figure 21:
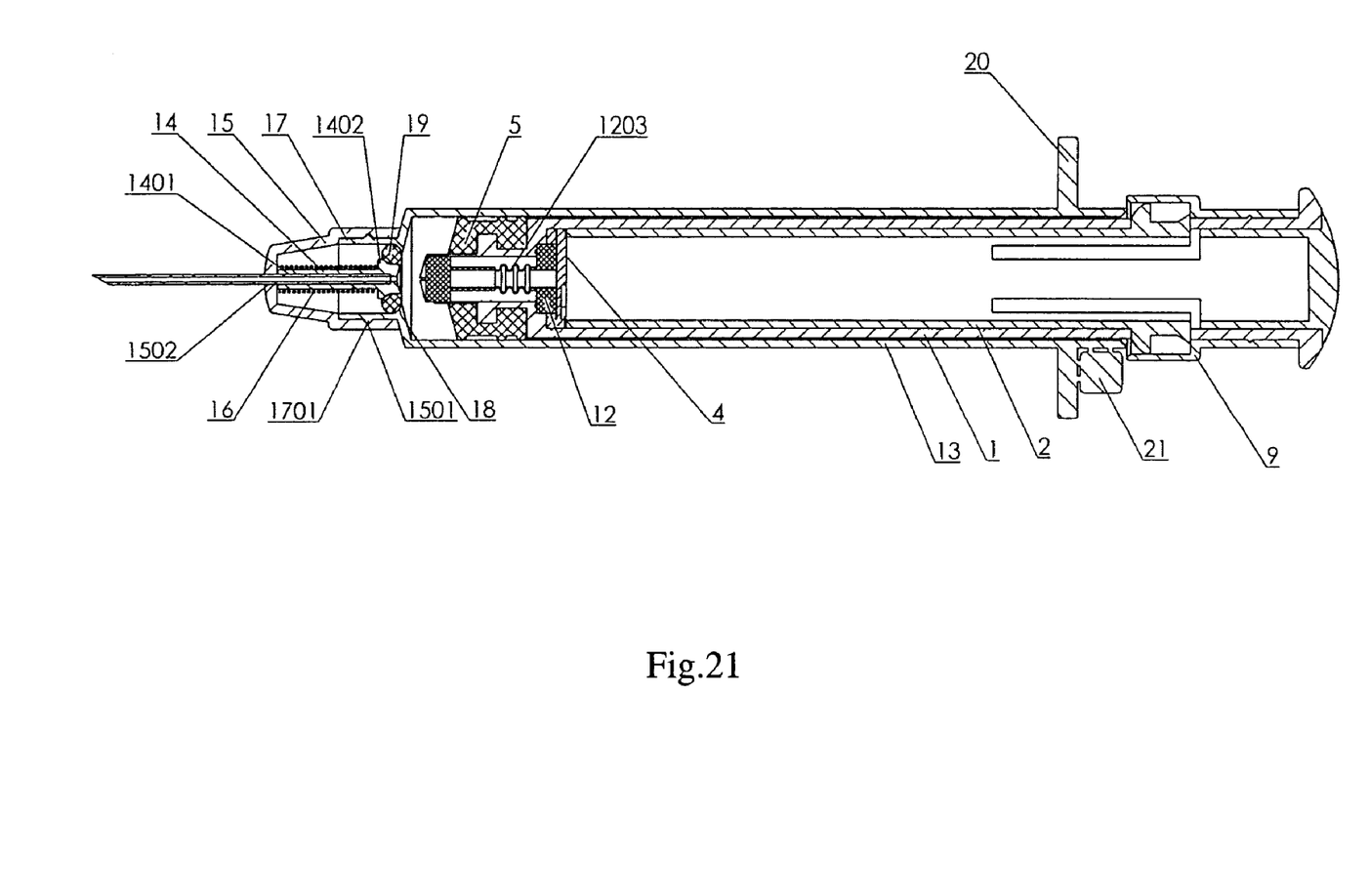
FIG. 21 is a section view of a safety injector according to one of the embodiments of the invention.

The forth embodiment: as shown in FIG. 21, the needle-retraction controllable safety injector according to this embodiment, comprises a needle syringe 13, a needle stand 14 for fixing a needle, a needle stand sheath 15, a spring 16, a needle stand fixture and a cylindrical pushrod as said in the third embodiment;

The needle syringe 13 forms a shoulder of contracting inward at its distal end, and the shoulder extends outward to form a cannula 17 with a less diameter than that of the needle syringe 13, the inside wall is provided with a round of flange 18 at the connection position of the shoulder with the cannula 17, and the outer wall of cannula 17 is provided with a round of flange 1701;

The needle stand 14 is a tubular body with a through hole 1401 in its center, the needle is fixed in the through hole 1401 of the needle stand 14, the lower end of needle stand 14 is provided with a dummy club 1402, and the needle stand 14 is installed within the cannula 17;

The needle stand fixture comprises a flange 18, a dummy club 1402 and an O-shape seal ring 19, the O-shape seal ring 19 is set around the lower portion of dummy club 1402 of the needle stand 14, the flange 18 supports the O-shape seal ring 19, and the O-shape seal ring 19 supports the dummy club 1402 of the needle stand 14, thereby the needle stand 14 is removably fixed in the cannula 17;

The spring 16 is set around the needle stand 14 with its lower end supported on the dummy club 1402 of the needle stand 14;

The needle stand sheath 15 has a hollow chamber opening rearward, the inner diameter of the chamber matches with the outer diameter of cannula 17, and the inside wall is provided with a round of groove 1501 clamping with the flange or groove 1701 on the outer wall of cannula 17, the closed top end of needle stand sheath 15 has a through hole 1502, the needle stand sheath 15 is installed on the cannula 17 mounted with the needle stand 14, the needle 1 extends out from the through hole 1502, the closed top end of needle stand sheath 15 press the upper end of spring 16 and prepress the spring 16 between the closed top end and the dummy club 1402 of the needle stand 14, and then the inferior border surface of the closed top end joints with the superior border surface of the top end of needle stand 14;

The cylindrical pushrod is installed within the needle syringe 13, the thick cylinder 901 of its protective sleeve 9 is connected around partly on the outer wall of the rear end of needle syringe 13, when the cylindrical pushrod is pushed to the top end of the chamber of needle syringe 13, the top end of cylindrical pushrod drives the O-shape seal ring 19 to slide as a whole or partially so as to loose the needle stand fixture and release the needle stand 14, at the same time, the inferior border surface of needle syringe 13 pushes to disengage the clamping structure of the rear end of the cylindrical pushrod and releases the inner cylinder 2;

A protective patch 21 is set between the roll rim 20 of the needle syringe 13 and the protective sleeve 9, the protective patch 21 is fixed on the inferior end surface of the roll 20 and on the cylinder wall of needle syringe 13.

Figure 22:
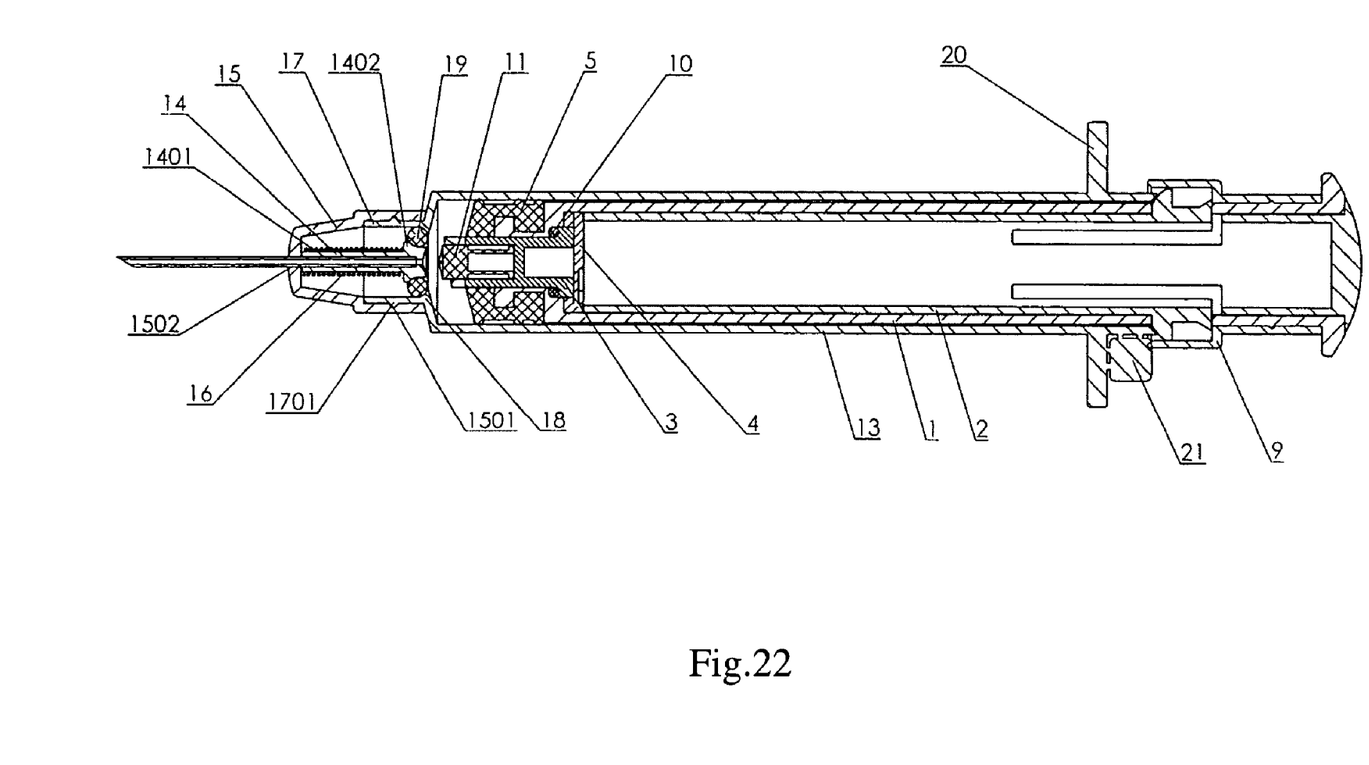
FIG. 22 is a section view of another safety injector according to the invention.

The fifth embodiment: as shown in FIG. 22, the basic structure of the needle-retraction controllable safety injector of this embodiment is similar to that of the forth embodiment, the difference include:

The said needle-retraction controllable safety injector comprises the cylindrical pushrod as said in the second embodiment.

I claim:

1. A cylindrical pushrod for the syringe needle-retracting safety injector, wherein the cylindrical pushrod comprises an outer cylinder, an inner cylinder, a push pole and an underpinned piece; the head of outer cylinder is provided with a sealing gasket; the push pole is set at the front end of chamber of outer cylinder, the front end of push pole closes the frontend opening of outer cylinder and outstands outside of the seal gasket, and appears as a tubular shape or projects partially in longitudinal direction, and the back end of said push pole is supported on the underpinned piece; the underpinned piece has a through hole for allowing the push pole to pass through and a underpinned patch for opening or closing the through hole, and the underpinned patch is set at the front end of the chamber of outer cylinder and supports the push pole; the inner cylinder is set inside the outer cylinder with its front end opened and its back end closed, and the top end surface of its cylinder wall supports the underpinned piece or the underpinned patch thereof to close the through hole; the tail of cylindrical pushrod is provided with a clamping structure for clamping the inner cylinder and the outer cylinder in a releasable manner, the clamping structure, after it is released, may make the inner cylinder slide backward to a distance for allowing the push pole pass through after opening the through hole under the action of retractive force of the needle, and is clamped within the outer cylinder again cylinder wall.

2. The cylindrical pushrod for the safety injector of pinhead retraction according to the claim 1, wherein the clamping structure is a supporting piece, which is composed of one O-shape ring part, two elastic strips and two raised blocks; the two elastic strips are set opposing to each other at both sides of the O-shape ring part; the two raised blocks are set respectively at the position on the outside of two elastic strips with the same height, and the two raised blocks are of the semispherical, triangle shape or the other shapes with a slope on its upside; the cylinder wall of outer cylinder is provided respectively with the holes having a matched shape with the raised blocks in the position matching with the two raised blocks; after the supporting piece is mounted, the two raised blocks engage into the holes respectively and protrude beyond the holes; the cylinder wall of rear portion of inner cylinder exists two long holes opposing to each other; the supporting piece is set around the rear portion of inner cylinder in the position of the long hole and engaged in the holes of outer cylinder, and the upper end of elastic strips supports the superior border's surface of the long hole of inner cylinder.

3. The cylindrical pushrod for the needle-retracting safety injector according to claim 1, wherein the cylinder wall of rear portion of the outer cylinder has at least one long hole; the cylinder wall of mid-back portion of inner cylinder has the corresponding long holes at the position matched with the long hole, the superior border of the long holes extends downward to form an upright or inclining outward elastic strips, and there are two raised blocks, the upper raised block and the lower raised block, on the outside wall of the elastic strips, the distance between the lower end surface of upper raised block and the lower end surface of lower raised block equals to or exceeds the distance of inner cylinder sliding backward for opening the through hole to allow the push pole passes through, the height of the upper raised block equals to or exceeds that of the lower raised block, and a slope is formed on the top thereof, the upper and lower raised blocks are fixed in and protrude outside the long holes, and the lower raised block is supported on the inferior border of the long hole so that the inner cylinder can be locked releasably on the outer cylinder.

4. The cylindrical pushrod for the needle-retracting safety injector according to claim 1, wherein the chamber of outer cylinder contracts inward to form a shoulder at the front end of outer cylinder, and extends forward to form a hollow chamber with a smaller diameter; the underpinned piece is a O-shape sheet with a through hole at its center, and is provided with a plurality of upwarping elastic underpinned patches; the underpinned piece is set at the front end of the chamber of outer cylinder, and the top end surface of inner cylinder pushes and presses the underpinned piece to the shoulder of the front end of chamber of outer cylinder to press down the elastic underpinned patchs which then occlude the through hole and support the push pole; the push pole is set in the hollow chamber with the smaller diameter at the front end of outer cylinder.

5. The cylindrical pushrod for the needle-retracting safety injector according to claim 1, wherein the underpinned piece is compose of a plug and an underpinned patch, the connection between the underpinned patch and the plug is a flexible connection, and a hinge structure, a gemel structure can be set between the underpinned patch and the plug, or the joint part can be formed as a flexional feeble layer, to realize the flexible connection between the two parts; an aperture through which the underpinned patch passes and which has a shape matching with the plug is provided on the cylinder wall of the front end of outer cylinder; after the underpinned patch is inserted into the aperture, the plug closes the aperture and secures one end of the underpinned patch on the cylinder wall of outer cylinder, the other end of the underpin patch is supported on the top end surface of the cylinder wall of inner cylinder.

6. The cylindrical pushrod for the needle-retracting safety injector according to claim 1, wherein the underpinned piece is a ring part, on which a through hole and an underpinned patch are provided, and a round of groove or flange playing the function of clamping is provided on its side wall, one end of the underpinned patch is free, and the other end of the underpinned patch connects to the underpinned piece flexibly; the underpinned piece is set at the front end of the chamber of outer cylinder, a round of flange or groove are provided on the cylinder wall of the front end of outer cylinder to match with the groove or flange on the underpinned piece, and the underpinned piece is fixed at the front end of chamber of outer cylinder through the clamping function of the groove and flange; the top end surface of the cylinder wall of inner cylinder supports the free end of the underpinned patch to close the through hole.

7. The cylindrical pushrod for the needle-retracting safety injector according to the claim 6, wherein it further comprises a protective sleeve which is a jointed body of a thick cylinder and a thin cylinder; a round of flange is set on the outer wall of the rear portion of outer cylinder; the inner diameter of thin cylinder matches with the outer diameter of outer cylinder, a round of groove is set on the inside wall of the thin cylinder to clamp with the flange, the protective sleeve is connected to the rear end of outer cylinder and is fixed by the clamping relation between the groove and the flange, the thick cylinder of the protective sleeve covers the clamping structure after being mounted.

8. A cylindrical pushrod for the safety injector of pinhead retraction according to the claim 7, wherein it further comprises a sealing gasket; the chamber of outer cylinder contracts inward to form a shoulder at the front end of outer cylinder, an annular dummy club is set at the lower end of push pole; the sealing gasket is mounted between the annular dummy club and the shoulder at the front end of the chamber of outer cylinder.

9. The cylindrical pushrod for the needle-retracting safety injector according to the claim 7, wherein the outer cylinder shows up a front end in a tubular shape or with partial longitudinal projection after the seal gasket is installed thereon; the push pole is changed into a compressible needle-stopping piece, the front end of the needle-stopping piece plugs into the opening of the hollow chamber of outer cylinder and has an exposed part at its front end which is higher than the front end of outer cylinder, the rear end of the needle-stopping is compressible and is supported on the underpinned piece, the compressive force of the needle-stopping piece exceeds or equals to the retractive force of the needle.

10. A needle-retraction controllable safety injector, wherein it comprises a needle syringe, a needle stand for fixing a needle, a needle stand sheath, a spring, a needle stand fixture and a cylindrical pushrod as said in claim 9; the needle syringe forms a shoulder of contracting inward at its distal end, and the shoulder extends outward to form a cannula with a less diameter than that of the needle syringe, the inside wall is provided with a round of flange at the connection position of the shoulder with the cannula, and the outer wall of cannula is provided with a round of flange or groove; the needle stand is a tubular body with a through hole in its center, the needle is fixed in the through hole of the needle stand, the lower end of needle stand is provided with a dummy club, and the needle stand is installed within the cannula; the said needle stand fixture comprises the flange, the dummy club and an O-shape seal ring, the said O-shape seal ring is set around the lower portion of dummy club of the needle stand, the flange supports the O-shape seal ring, and the O-shape seal ring supports the dummy club of the needle stand, thereby the needle stand is removably fixed in the cannula; the spring is set around the needle stand with its lower end supported on the dummy club of the needle stand; the needle stand sheath has a hollow chamber opening rearward, the inner diameter of the chamber matches with the outer diameter of cannula, and the inside wall is provided with a round of groove or flange clamping with the flange or groove on the outer wall of cannula, the closed top end of needle stand sheath has a through hole, the needle stand sheath is installed on the cannula mounted already with the needle stand, the needle extendes out from the through hole, the closed top end of needle stand sheath press the upper end of spring and prepress the spring between the closed top end and the dummy club of the needle stand, and then the lower border surface of the closed top end joints with the upper border surface of the top end of needle stand; the said cylindrical pushrod is installed within the needle syringe, the thick cylinder of its protective sleeve is connected around partly on the outer wall of the rear end of needle syringe, when the cylindrical pushrod is pushed to the top end of the chamber of needle syringe, the top end of cylindrical pushrod drives the O-shape seal ring to slide as a whole or partially so as to loose the needle stand fixture and release the needle stand, at the same time, the lower border surface of needle syringe push to disengage the clamping structure of the rear end of the cylindrical pushrod and releases the inner cylinder.

11. The cylindrical pushrod for the needle-retracting safety injector according to the claim 9, wherein the needle-stopping piece is composed of a piston head and a compressible part; the piston head plugs into the opening of the hollow chamber of outer cylinder and has an exposed part which is higher than the front end of outer cylinder; the compressible part may be a hollow thinwall pipe or a hollow corrugated pipe, and also may be a spring supporting the piston head.

12. The cylindrical pushrod for the needle-retracting safety injector according to the claim 11, wherein the rear end of the needle-stopping piece is provided with a supporting dummy club which matches with the shoulder positioned at the top end of chamber of the outer cylinder.

13. The cylindrical pushrod for the needle-retracting safety injector according to the claim 11, wherein on the top surface of needle-stopping piece is provided with a groove; a slot communicated with the groove is provided on the cylinder wall at the front end of outer cylinder.

14. A needle-retraction controllable safety injector, wherein it comprises a needle syringe, a needle stand for fixing a needle, a needle stand sheath, a spring, a needle stand fixture and a cylindrical pushrod as said in claim 13; the needle syringe forms a shoulder of contracting inward at its distal end, and the shoulder extends outward to form a cannula with a less diameter than that of the needle syringe, the inside wall is provided with a round of flange at the connection position of the shoulder with the cannula, and the outer wall of cannula is provided with a round of flange or groove; the needle stand is a tubular body with a through hole in its center, the needle is fixed in the through hole of the needle stand, the lower end of needle stand is provided with a dummy club, and the needle stand is installed within the cannula; the said needle stand fixture comprises the flange, the dummy club and an O-shape seal ring, the said O-shape seal ring is set around the lower portion of dummy club of the needle stand, the flange supports the O-shape seal ring, and the O-shape seal ring supports the dummy club of the needle stand, thereby the needle stand is removably fixed in the cannula; the spring is set around the needle stand with its lower end supported on the dummy club of the needle stand; the needle stand sheath has a hollow chamber opening rearward, the inner diameter of the chamber matches with the outer diameter of cannula, and the inside wall is provided with a round of groove or flange clamping with the flange or groove on the outer wall of cannula, the closed top end of needle stand sheath has a through hole, the needle stand sheath is installed on the cannula mounted already with the needle stand, the needle extends out from the through hole, the closed top end of needle stand sheath press the upper end of spring and prepress the spring between the closed top end and the dummy club of the needle stand, and then the lower border surface of the closed top end joints with the upper border surface of the top end of needle stand; the said cylindrical pushrod is installed within the needle syringe, the thick cylinder of its protective sleeve is connected around partly on the outer wall of the rear end of needle syringe, when the cylindrical pushrod is pushed to the top end of the chamber of needle syringe, the top end of cylindrical pushrod drives the O-shape seal ring to slide as a whole or partially so as to loose the needle stand fixture and release the needle stand, at the same time, the lower border surface of needle syringe push to disengage the clamping structure of the rear end of the cylindrical pushrod and releases the inner cylinder.

15. The needle-retraction controllable safety injector according to the claim 14, wherein a protective patch is provided between the roll rim of the needle syringe and the protective sleeve to prevent the cylindrical pushrod from being pushed to the top end of the chamber of needle syringe and the needle stand and the clamping structure being loosed prior to the use of the injector due to a misoperation; the protective patch can be fixed on the lower end surface of the roll rim, and also can be fixed on the cylinder wall of the needle syringe or the protective sleeve.

16. The cylindrical pushrod for the needle-retracting safety injector according to claim 1, wherein it further comprises a compressible needle-stopping piece; a hollow chamber is set at the front end of push pole; the needle-stopping piece is set within the hollow chamber at the front end of push pole, the needle-stopping piece has an exposed part at the front end which is higher than the front end of push pole after plugging the opening of the hollow chamber of push pole, and the compressive force of the needle-stopping piece is larger than or equal to the retractive force of the needle.

17. The cylindrical pushrod for the needle-retracting safety injector according to the claim 16, wherein the needle-stopping piece is composed of a piston head and a compressible part, the compressible part may be a hollow thinwall pipe or a hollow corrugated pipe, and also may be a spring supporting the piston head.

18. The cylindrical pushrod for the needle-retracting safety injector according to the claim 17, wherein a groove is set on the top surface of the needle-stopping piece; a slot communicated with the groove is set in the chamber wall of the hollow chamber at the front end of push pole.

19. A needle-retraction controllable safety injector, wherein it comprises a needle syringe, a needle stand for fixing a needle, a needle stand sheath, a spring, a needle stand fixture and a cylindrical pushrod as said in claim 18; the needle syringe forms a shoulder of contracting inward at its distal end, and the shoulder extends outward to form a cannula with a less diameter than that of the needle syringe, the inside wall is provided with a round of flange at the connection position of the shoulder with the cannula, and the outer wall of cannula is provided with a round of flange or groove; the needle stand is a tubular body with a through hole in its center, the needle is fixed in the through hole of the needle stand, the lower end of needle stand is provided with a dummy club, and the needle stand is installed within the cannula; the said needle stand fixture comprises the flange, the dummy club and an O-shape seal ring, the said O-shape seal ring is set around the lower portion of dummy club of the needle stand, the flange supports the O-shape seal ring, and the O-shape seal ring supports the dummy club of the needle stand, thereby the needle stand is removably fixed in the cannula; the spring is set around the needle stand with its lower end supported on the dummy club of the needle stand; the needle stand sheath has a hollow chamber opening rearward, the inner diameter of the chamber matches with the outer diameter of cannula, and the inside wall is provided with a round of groove or flange clamping with the flange or groove on the outer wall of cannula, the closed top end of needle stand sheath has a through hole, the needle stand sheath is installed on the cannula mounted already with the needle stand, the needle extends out from the through hole, the closed top end of needle stand sheath press the upper end of spring and prepress the spring between the closed top end and the dummy club of the needle stand, and then the lower border surface of the closed top end joints with the upper border surface of the top end of needle stand; the said cylindrical pushrod is installed within the needle syringe, when the cylindrical pushrod is pushed to the top end of the chamber of needle syringe, the top end of cylindrical pushrod drives the O-shape seal ring to slide as a whole or partially so as to loose the needle stand fixture and release the needle stand, at the same time, the lower border surface of needle syringe push to disengage the clamping structure of the rear end of the cylindrical pushrod and releases the inner cylinder.

20. A needle-retraction controllable safety injector, wherein it comprises a cylindrical pushrod for the needle-retracting safety injector as set forth in claim 1.

* * * * *